(12) United States Patent
Asconeguy

(10) Patent No.: US 8,858,548 B2
(45) Date of Patent: Oct. 14, 2014

(54) INDEPENDENT PASSIVE COOLING DESIGN FOR ABLATION CATHETERS

(75) Inventor: Alexander J. Asconeguy, Murrieta, CA (US)

(73) Assignee: Medtronic Ablation Frontiers LLC, Minneapolis, MN (US)

( * ) Notice: Subject to any disclaimer, the term of this patent is extended or adjusted under 35 U.S.C. 154(b) by 863 days.

(21) Appl. No.: 13/048,558

(22) Filed: Mar. 15, 2011

(65) Prior Publication Data

US 2012/0239019 A1  Sep. 20, 2012

(51) Int. Cl.
  *A61B 18/12* (2006.01)
  *A61B 18/14* (2006.01)
  *A61B 18/00* (2006.01)

(52) U.S. Cl.
  CPC ... *A61B 18/1492* (2013.01); *A61B 2018/00702* (2013.01); *A61B 2018/00577* (2013.01); *A61B 2018/00351* (2013.01); *A61B 2018/00791* (2013.01); *A61B 2018/00023* (2013.01)
  USPC .......................................................... 606/41

(58) Field of Classification Search
  USPC .......................................... 606/20–27, 34, 41
  See application file for complete search history.

(56) References Cited

U.S. PATENT DOCUMENTS

| | | | |
|---|---|---|---|
| 5,281,217 A | 1/1994 | Edwards et al. | |
| 5,423,807 A * | 6/1995 | Milder ............................ | 606/20 |
| 5,545,161 A * | 8/1996 | Imran ............................. | 606/41 |
| 5,891,138 A * | 4/1999 | Tu et al. ......................... | 606/41 |
| 6,505,629 B1 | 1/2003 | Mikus et al. | |
| 6,611,699 B2 | 8/2003 | Messing | |
| 6,730,077 B2 | 5/2004 | Carroll et al. | |
| 7,238,184 B2 | 7/2007 | Megerman et al. | |
| 2004/0181214 A1 | 9/2004 | Garabedian et al. | |
| 2006/0052778 A1* | 3/2006 | Chapman et al. ............... | 606/51 |
| 2006/0089635 A1* | 4/2006 | Young et al. .................... | 606/41 |
| 2007/0073285 A1* | 3/2007 | Peterson ......................... | 606/41 |
| 2008/0125764 A1 | 5/2008 | Vancelette et al. | |
| 2009/0149930 A1 | 6/2009 | Schenck | |
| 2009/0254078 A1 | 10/2009 | Just et al. | |
| 2009/0318850 A1 | 12/2009 | Schenck | |
| 2010/0262135 A1 | 10/2010 | Berube | |
| 2011/0022041 A1 | 1/2011 | Ingle et al. | |

FOREIGN PATENT DOCUMENTS

| | | |
|---|---|---|
| WO | 9202272 A1 | 2/1992 |
| WO | 0174442 A1 | 10/2001 |
| WO | 03039338 A2 | 5/2003 |
| WO | 2007008954 A2 | 1/2007 |

* cited by examiner

Primary Examiner — Michael Peffley
Assistant Examiner — Daniel Fowler
(74) Attorney, Agent, or Firm — Christopher & Weisberg, P.A.

(57) ABSTRACT

A medical system, including a catheter having a fluid flow path and a distal portion separated from the fluid flow path; a plurality of electrodes coupled to the distal portion; at least one temperature sensor coupled to the distal portion; a heat sink in thermal communication with each electrode and in fluid communication with the fluid flow path; a radiofrequency signal generator in communication with the plurality of electrodes; and a fluid source in fluid communication with the fluid flow path.

20 Claims, 4 Drawing Sheets

INDEPENDENT PASSIVE COOLING DESIGN FOR ABLATION CATHETERS

CROSS-REFERENCE TO RELATED APPLICATION n/a

STATEMENT REGARDING FEDERALLY SPONSORED RESEARCH OR DEVELOPMENT n/a

FIELD OF THE INVENTION

The present invention relates to systems and methods of use thereof for controlling temperature of medical devices, and in particular, toward cooling catheter electrodes.

BACKGROUND OF THE INVENTION

Minimally invasive devices are often employed for medical procedures, including those involving ablation, dilation, and the like. In a particular situation, an ablation procedure on may involve creating a series of inter-connecting or otherwise contiguous lesions in order to electrically isolate tissue believed to be the source of an arrhythmia. Such lesions may be created using a variety of different energy transmission modalities, such as cryogenic freezing or heating with radiofrequency ("RF") energy, for example.

Radiofrequency or other ablation devices often include one or more electrically conductive surfaces or electrodes to impart electrical or thermal energy conduction through a tissue site. During operation, the tissue heats up, thus heating the electrodes that are in tissue contact. When positioned in anatomical areas that have high fluid (blood, etc.) flow, a portion of the electrodes are cooled via convection with the passing fluid, thus dissipating heat as tissue is ablated. The portions of the electrodes engaged with the tissue are typically not exposed to the surrounding fluid flow, and as a result, are not cooled to the same degree. Indeed, the contacted surface of the electrodes are heated through conduction by the tissue itself as it is ablated, and a temperature sensor in contact with this section of the electrode or tissue could provide an accurate tissue/electrode interface temperature. This ability to accurately measure the tissue/electrode interface temperature can be used as a means of feedback to control the energy being applied through the electrodes and to the tissue. Exceeding a particular temperature range or threshold can result in unwanted injury to the tissue site, including tissue charring, and can also compromise the medical device itself.

When an ablation device is located in an area of little or no physiological fluid flow, the ability for the electrode to dissipate heat is hampered, which limits the delivery of ablation energy modulated by a measured temperature response, e.g., the temperature rises more quickly, which may require a quicker reduction in the powering of the device and thus, reduced treatment efficacy. Current ablation systems that deal in this temperature-response regime sometimes rely on other measured responses (e.g. impedance) as an alternate means of control loop feedback, or can operate in a feed-forward control mode (e.g. set the ablation energy source to a fixed power setting). However, by not relying on the tissue/electrode interface temperature, the latter two methods of treatment control can again invite the undesired injury resulting from excess heat generated by the tissue.

To supplement cooling a device operating in an area having little physiological fluid flow, the delivery of an irrigation or cooling fluid is sometimes utilized (e.g., irrigated radio frequency ablation catheters and similar actively cooled devices). The design intent of active cooling is to allow the ablation electrode(s) to dissipate heat in low or no flow areas of the heart or other anatomy by flooding or circulating the electrode with saline or other cooling fluid. Unfortunately, such irrigated devices and methods cannot rely on dynamic temperature measurement as a means of feedback control because when the ablation electrode or surface is cooled directly, a temperature sensor in contact with ablation electrode is also subjected to the cooling fluid, which compromises its ability to accurately measure the actual temperature at the electrode/tissue interface. The compromised accuracy of the temperature measurements again invites injury from excessive heat buildup.

In view of the above, it is desirable to provide effective cooling mechanisms for medical devices used in environments having low fluid flow rates or reduced ambient cooling without compromising the ability to accurately measure or monitor temperature of a device-tissue interface for control or operation of the device.

SUMMARY OF THE INVENTION

The present disclosure advantageously provides effective cooling mechanisms for medical devices used in environments having low fluid flow rates or reduced ambient cooling without compromising the ability to accurately measure or monitor temperature of a device-tissue interface for control or operation of the device.

In particular, a medical device is provided, including an elongate body defining a fluid flow path through at least a portion thereof; at least one electrode disposed on the elongate body; a temperature sensor proximate the electrode; and a heat transfer element defining a first portion in thermal communication with the electrode and a second portion in thermal communication with the fluid flow path, where at least one of the electrode and temperature sensor is isolated from the fluid flow path. The heat transfer element may include an elongated heat sink; and/or may be asymmetrically positioned about a longitudinal axis of the elongate body. The fluid flow path may include a fluid injection conduit and a fluid exhaust lumen, and a coolant source, such as a cryogenic fluid, may be coupled to the fluid flow path. The device may include a vacuum source coupled to the fluid flow path; and/or an electrical power source coupled to the electrode, where the electrical power source is a radiofrequency signal generator.

A medical system is provided, including a catheter having a proximal portion and a distal portion; a plurality of electrodes on the distal portion; at least one temperature sensor coupled to the distal portion; an elongate heat transfer element in thermal communication with each electrode; and a radiofrequency signal generator in communication with the plurality of electrodes, the radiofrequency signal generator programmed to modulate radiofrequency energy delivery to the plurality of electrodes based at least in part on a signal from the at least one temperature sensor. The distal portion may define a tissue contact side, and a non-contact side opposite the tissue contact side, and where the elongate heat transfer element may be positioned adjacent the non-contact side. The heat transfer element may be asymmetrically positioned about a longitudinal axis of the catheter. The system may include a fluid injection tube disposed within the catheter; a fluid exhaust lumen disposed within the catheter; and a fluid source connected to the fluid injection tube, where the distal portion is not in fluid communication with the fluid injection tube; the plurality of electrodes are not in fluid communication with the fluid injection tube; and/or the at least one temperature sensor is not in fluid communication with the fluid injection tube.

A medical system is provided, including a catheter having a fluid flow path and a distal portion separated from the fluid flow path; a plurality of electrodes coupled to the distal portion; at least one temperature sensor coupled to the distal portion; a heat sink in thermal communication with each electrode and in fluid communication with the fluid flow path; a radiofrequency signal generator in communication with the plurality of electrodes. The heat sink may be asymmetrically positioned about a longitudinal axis of the catheter; the radiofrequency signal generator may be programmed to adjust radiofrequency energy delivery to the plurality of electrodes based at least in part on feedback from the at least one temperature sensor; and/or the system may include a fluid source in fluid communication with the fluid flow path.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
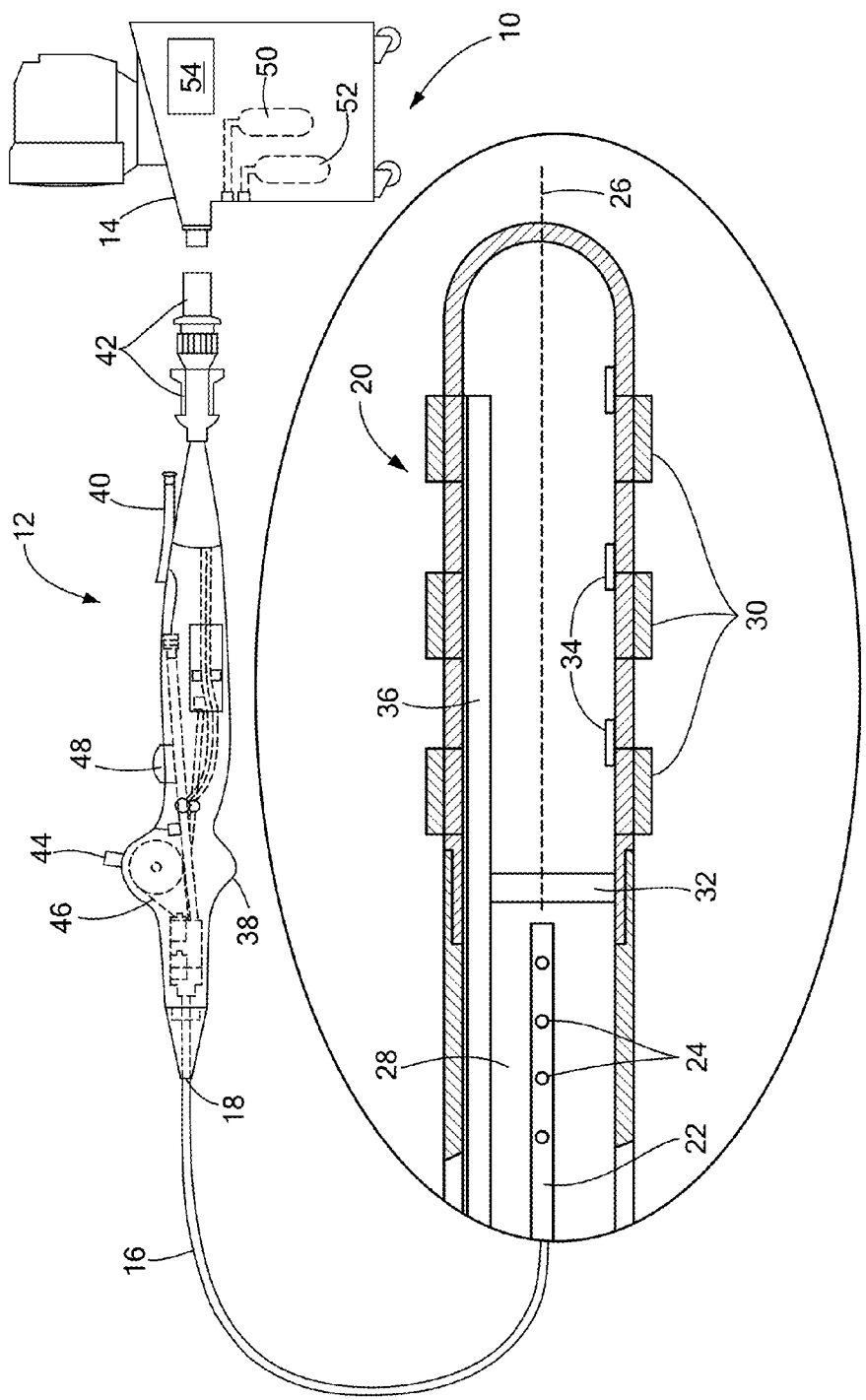
FIG. 1 is an illustration of an exemplary medical system constructed in accordance with the principles of the present invention.

The present invention disclosure advantageously provides effective cooling mechanisms for medical devices used in environments having low fluid flow rates or reduced ambient cooling without compromising the ability to accurately measure or monitor temperature of a device-tissue interface for control or operation of the device. Referring now to the drawing figures in which like reference designations refer to like elements, an embodiment of a medical system constructed in accordance with principles of the present invention is shown in FIG. 1 and generally designated as "10." The system 10 generally includes a medical device 12 that may be coupled to a control unit 14 or operating console. The medical device 12 may generally include one or more diagnostic or treatment regions for energetic, therapeutic and/or investigatory interaction between the medical device 12 and a treatment site. The treatment region(s) may deliver, for example, cryogenic therapy, radiofrequency energy, electroporation treatment or other energetic transfer with a tissue area in proximity to the treatment region(s), including cardiac tissue, tumors, or other undesired growths or structures.

Continuing to refer to FIG. 1, the medical device 12 may include an elongate body 16 passable through a patient's vasculature and/or proximate to a tissue region for diagnosis or treatment, such as a catheter, sheath, or intravascular introducer. The elongate body 16 may define a proximal portion 18 and a distal portion 20, and may further include one or more lumens disposed within the elongate body 16 thereby providing mechanical, electrical, and/or fluid communication between the proximal portion 18 of the elongate body 16 and the distal portion 20 of the elongate body 16, as discussed in more detail below.

For example, the medical device 12 may include a fluid delivery or injection conduit 22 traversing at least a portion of the elongate body. The fluid delivery conduit 22 may define a lumen therein for the passage or delivery of a fluid from the proximal portion of the elongate body 16 and/or the control unit 14 to the distal portion 20 and/or treatment region of the medical device 12. The fluid delivery conduit 22 may further include one or more apertures or openings 24 therein, to provide for the dispersion or directed ejection of fluid from the lumen to an environment exterior to the fluid delivery conduit. For example, the fluid delivery conduit 22 may define one or more ports or valves movably positionable with respect to the elongate body 16. The fluid delivery conduit 22 and the port(s) may be both rotatable about a longitudinal axis 26 of the elongate body 16, and may further be longitudinally positionable or slidable along the at least a portion of the length of the elongate body 16. The rotational and slidable orientation of the fluid delivery conduit 22 allows for the controlled, directional dispersion of fluid from the delivery conduit 22 towards a particular segment or region of the medical device 12.

The medical device 12 may further include an exhaust lumen or conduit 28 providing an evacuation path for fluid dispersed or otherwise present within the medical device 12. The exhaust lumen 28 may be defined by a wall of the elongate body 16 itself, or by another auxiliary tube or conduit disposed within at least a portion of the medical device 12. The exhaust lumen 28 may be in fluid communication with a proximal portion of the elongate body 16 and/or the medical device 12 to allow access and/or coupling of the exhaust lumen 28 to the control unit 14 for removal, storage, and/or recirculation of a fluid exiting the exhaust lumen. The exhaust lumen 28 and the fluid delivery conduit 22 may thus provide a fluid flow path through at least a portion of the medical device 12.

The distal portion 20 of the medical device 12 may include one or more electrically conductive portions or electrodes 30 thereon coupled to a radiofrequency generator or power source. In particular, a plurality of electrodes or electrically conductive portions 30 may be disposed on or otherwise situated about the distal portion 20 of the elongate body 16. The electrodes 30 may be isolated or separated from the fluid path coursing through the elongate body 16. For example, the medical device 12 may include a wall or other fluidically-sealing component 32 that separates the distal portion 20 of the medical device from a proximal region or compartment of the elongate body 16. The distal portion 20, and the electrodes 30, may thus be excluded from receiving or being subjected to any fluid dispersion or circulation therethrough, while a more-proximal region or compartment of the medical device 12 and/or elongate body 16 receives or is otherwise subject to dispersed fluid circulation.

The electrodes 30 may include variations in their number, arrangement, configuration, or shape. For example, the electrodes 30 may be in the form of conductive strips applied to the outer surface of the elongate body 16. The electrodes 30 may consist of hollow cylindrical rings adhesively bonded to the elongate body 16 to circumscribe a longitudinal axis 26 thereof, e.g., the electrodes 30 may be substantially coaxial with the elongate body 16. The electrodes 30 may be positioned at discrete, spaced locations on the distal portion 20, and may surround or encircle substantially all or only a fractional portion of the elongate body 16. The electrodes 30 may be made of metal, conductive polymers, conductive ink printing, or the like to provide sufficient electrical and/or thermal conductivity during the operation of the medical device 12. The electrodes 30 may be arranged at different angular positions around the elongate body 16 and/or the medical device 12.

The medical device 14 may further include one or more temperature sensors 34 proximate the distal portion 20 and/or electrodes 30 for monitoring, recording or otherwise conveying measurements or conditions within the medical device 12, the ambient environment at the distal portion 20 of the medical device 12, and/or an interface or junction between the device and a contacted tissue surface. For example, the temperature sensor(s) 34 may include a thermistor coupled to one or more of the electrodes 30. The temperature sensor(s) 34 may also be positioned adjacent an electrode 30 at the distal portion 20 of the medical device 12, and may be embedded into a surface of the elongate body 16, for example. The one or more temperature sensors 34 may be asymmetrically disposed about the elongate body 16 and/or distal portion 20 to align along a surface or region of the medical device 12 that is steered, directed, or otherwise manipulated into contact with a tissue site. Similar to the electrodes 30 discussed above, the temperature sensor placement in the distal portion 20 of the elongate body 16 may seclude the sensors from any fluid flow or dispersion occurring in more-proximate regions of the elongate body 16. The sensor(s) 34 may be in communication with the control unit 14 for initiating or triggering one or more alerts or therapeutic delivery modifications during operation of the medical device 12.

Figure 2:
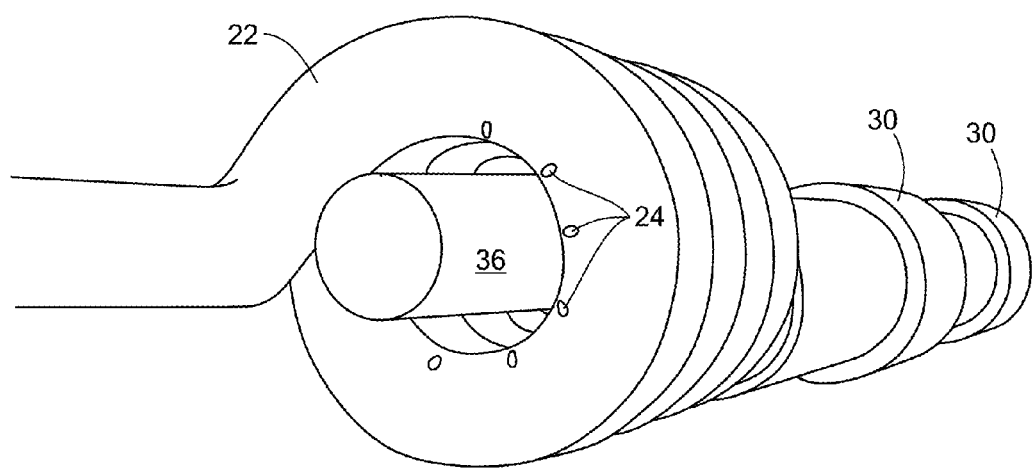
FIG. 2 is an illustration of a medical device constructed in accordance with the principles of the present invention.

The medical device 12 may include a heat transfer element 36 at least partially disposed within the distal portion 20 of the elongate body 16 that provides a thermal conduit to remove heat from one or more components at the distal portion 20, such as the electrodes 30. For example, the heat transfer element 36 may include a heat sink, an elongated mandrel, or other thermally-conductive body in thermal communication with one or more of the electrodes 30. The heat transfer element 36 may be bonded, fused or otherwise coupled to one or more of the electrodes 30 to enhance or facilitate thermal communication therebetween. In addition to being in thermal communication and/or direct coupling to one or more of the electrodes 30, the heat transfer element 36 may also be at least partially disposed within or subject to the fluid flow path through the elongate body 16. For example, the heat transfer element 36 may extend through the wall 32 to define a portion adjacent or in proximity to the ports or apertures of the fluid delivery conduit 22. In another example, a portion of the fluid delivery conduit 22 may be coiled or helically wrapped around a portion of the heat transfer element 36 with the fluid delivery ports 24 concentrated towards the heat transfer element 36, as shown in FIG. 2. As a result, fluid dispersed from the fluid delivery conduit 22 may be directed towards the exposed portion of the heat transfer element 36, while the wall 32 or other features of the elongate body 16 prevents fluid flow from travelling distally towards the electrodes 30 and/or temperature sensors 34.

The heat transfer element 36 may be asymmetrically disposed within a portion of the elongate body 16. For example, the heat transfer element 36 may be aligned or oriented adjacent a surface of the elongate body 16 opposite where the elongate body 16 and/or electrodes 30 may contact a tissue surface. The heat transfer element 36 may thus be aligned on a surface or side of a longitudinal axis 26 of the medical device oppositely of the temperature sensors 34 that, as discussed above, may be aligned adjacent a tissue-contacting surface of the device 12.

Continuing to refer again to FIG. 1, the medical device 12 may include a handle 38 coupled to the proximal portion of the elongate body 16. The handle 38 can include circuitry for identification and/or use in controlling of the medical device 12 or another component of the system 10. Additionally, the handle 38 may be provided with a fitting 40 for receiving a guide wire or another diagnostic/treatment instrument (not shown). The handle 38 may also include connectors 42 that are matable to the control unit 14 to establish communication between the medical device 12 and one or more components or portions of the control unit 14.

The handle 38 may also include one or more actuation or control features that allow a user to control, deflect, steer, or otherwise manipulate a distal portion of the medical device 12 from the proximal portion of the medical device 12. For example, the handle 38 may include one or more components such as a lever or knob 44 for manipulating the elongate body 16 and/or additional components of the medical device 12. For example, a pull wire 46 with a proximal end and a distal end may have its distal end anchored to the elongate body 16 at or near the distal portion 20. The proximal end of the pull wire 46 may be anchored to an element such as a cam in communication with and responsive to the lever 44.

The medical device 12 may include an actuator element 48 that is movably coupled to the proximal portion of the elongate body 16 and/or the handle 38 for the manipulation and movement of a portion of the medical device 12, such as the fluid delivery conduit and/or distal portion, for example. The actuator element 48 may include a thumb-slide, a push-button, a rotating lever, or other mechanical structure for providing a movable coupling to the elongate body 16 and/or the handle. Moreover, the actuator element 48 may be movably coupled to the handle 38 such that the actuator element 48 is movable into individual, distinct positions, and is able to be releasably secured in any one of the distinct positions.

Although illustrated as substantially linear, the distal portion 20 of the medical device 12 may be configured into a variety of geometric configurations. The distal portion 20 and/or relate components of the medical device may be flexible or malleable to take on virtually any desired shape. For example, manipulating the shape or configuration of the distal portion 20, the arrangement of the electrodes 30, or the like may be achieved at least in part through one or more controls at the handle 38 as described herein.

The system 10 may include one or more treatment or diagnostic sources coupled to the medical device 12 for use in an operative procedure, such as tissue ablation, for example. The control unit 14 may include a fluid supply 50 including a coolant, cryogenic refrigerant, or the like, an exhaust or scavenging system (not shown) for recovering or venting expended fluid for re-use or disposal, as well as various control mechanisms. In addition to providing an exhaust function for the fluid or coolant supply, the control unit 14 may also include pumps, valves, controllers or the like to recover and/or re-circulate fluid delivered from the fluid supply 50 to the handle 38, the elongate body 16, and/or the fluid pathway(s) of the medical device 12. A vacuum pump 52 in the control unit 14 may create a low-pressure environment in one or more conduits within the medical device 12, such as the exhaust lumen 28, so that fluid is drawn into the conduit(s)/lumen(s) of the elongate body 16, away from the distal portion 20 and towards the proximal portion 18 of the elongate body 16.

The console 12 may also include a radiofrequency signal generator or power source 54 in electrical communication with the electrodes 30. The generator 54 may include a plurality of output channels, with each channel coupled to an individual electrode or electrically conductive surface 30 of the medical device 12. The generator 54 may be operable in one or more modes of operation, including for example: (i) bipolar energy delivery between at least two electrodes 30 or electrically-conductive portions of the medical device 12 within a patient's body, (ii) monopolar or unipolar energy delivery to one or more of the electrodes 30 or electrically-conductive portions on the medical device 12 within a patient's body and through a patient return or ground electrode (not shown) spaced apart from the electrodes 30 of the medical device 12, such as on a patient's skin for example, and (iii) a combination of the monopolar and bipolar modes.

The system 10 may further include one or more sensors to monitor the operating parameters throughout the system 10, including for example, pressure, temperature, flow rates, volume, power delivery, impedance, or the like in the control unit 14 and/or the medical device 12, in addition to monitoring, recording or otherwise conveying measurements or conditions within the medical device 12 or the ambient environment at the distal portion of the medical device 12. The sensor(s) may be in communication with the control unit 14 for initiating or triggering one or more alerts or therapeutic delivery modifications during operation of the medical device 12. One or more valves, controllers, or the like may be in communication with the sensor(s) to provide for the controlled dispersion or circulation of fluid through the lumens/fluid paths of the medical device 12. Such valves, controllers, or the like may be located in a portion of the medical device 12 and/or in the control unit 14. The control unit 14 may include one or more controllers, processors, and/or software modules containing instructions or algorithms to provide for the automated operation and performance of the features, sequences, calculations, or procedures described herein.

Figure 3:
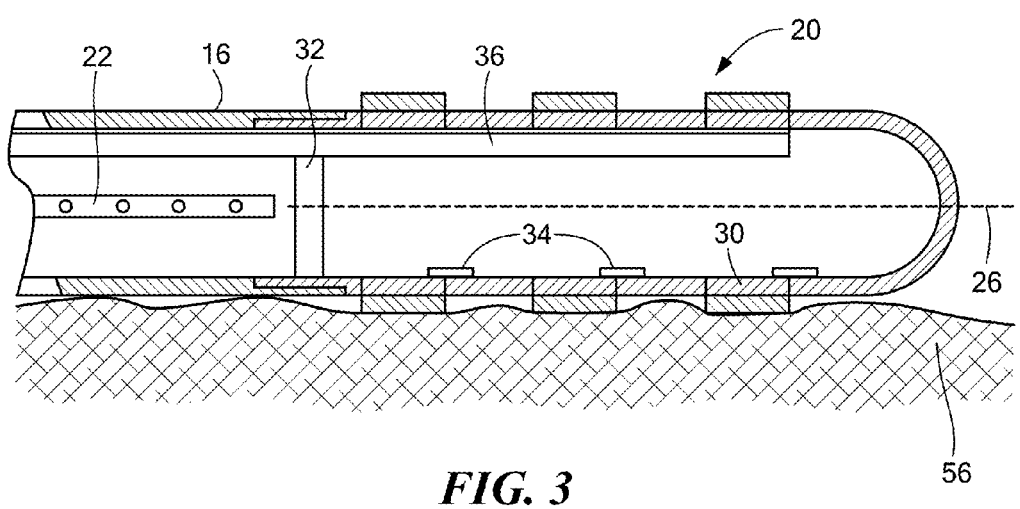
FIG. 3 is an illustration of an exemplary us of the medical system shown in FIG. 1.

Now referring to FIG. 3, in an exemplary method of use, the medical system 10 may be used to deliver therapeutic treatment, such as ablation treatment for example, to a targeted tissue area 56, which may include a targeted tissue region in the heart, a tumor, or other diagnosed region slated for treatment. The distal portion 20 may be positioned in the proximity of the targeted tissue area 56. Such positioning may be aided or facilitated by visualization methods including fluoroscopy or the like as known in the art. Once the medical device 12 is positioned in the desired location, the system 10 may be operated to thermally affect the targeted tissue. In particular, the electrodes 30 may deliver radiofrequency energy treatment to the targeted tissue to achieve the desired therapeutic effect, such as the controlled ablation of problematic tissue to an effective depth within the targeted tissue region. Powering of the electrodes 30 may include delivery of a radiofrequency signal or current form the radiofrequency generator 54 resulting in a current flow, and thus heating, between one or more of the electrodes 30 either between each other (e.g., bipolar RF delivery) or to a ground/patient electrode (not shown) in unipolar or monopolar operation. The electrodes 30 may be powered ablate or otherwise treat tissue until a preselected temperature or power delivery threshold has been reached. The predefined temperature or power delivery threshold may be selected to ensure that the affected tissue is not charred or otherwise heated to an undesirable degree.

Operation of the electrodes 30 will result in rising temperatures both in the tissue and in the electrodes 30, which may be monitored by one or more of the temperature sensors. As discussed above, information from the temperature sensors 34 may be relayed to the control unit 14, which, in turn, modulates or adjusts the energy delivery to the electrodes 30 to avoid excessive heat buildup and associated injury to the patient. The control unit 14 may, for example, reduce a current or voltage delivered to the electrodes 30, or may extend on "off" period of the electrodes 30 should they be powered by a series of duty cycles.

The heat generated at the electrode-tissue interface will at least partially dissipate through the surrounding tissue and through any ambient fluid flow passing over the electrodes 30 and/or other parts of the medical device 12. In addition, the heat transfer element 36 provides cooling capacity to dissipate and remove heat from the electrodes 30. The heat transfer element 36 is in thermal communication with the electrodes 30, and thus, as temperature rises at the electrodes 30, the heat will flow to the heat transfer element 36 and raise its temperature. To decrease the raises in temperature, a fluid or coolant may be introduced into the fluid flow path of the medical device 12. In particular, coolant may be transferred from the fluid source 50 in the control unit to the fluid delivery conduit 22. The fluid may be ejected through one of the ports in the fluid delivery conduit 22, where the ejection may include a phase change from liquid to gas to provide increased cooling capacity. The discharge may be in proximity to the heat transfer element 36, and indeed, may be directed specifically towards the heat transfer element 36. The dispersed fluid may then be evacuated through the exhaust 28 lumen by the vacuum source 52.

The fluid flow may be intermittently provided in pulsed flow, or may be continuously circulated through the flow path. Further, the control unit 14 may modulate fluid flow by varying pressure, flow rates, or the like in direct response to the measured temperatures in the distal portion 20 as relayed by the temperature sensors 34. For example, upon reaching a preselected temperature threshold or range at the tissue interface, in addition to modulating power delivery to the electrodes 30, fluid flow through the fluid flow path may be increased or decreased accordingly to substantially maintain a target temperature at the distal portion 20 of the device 12.

Figure 4:
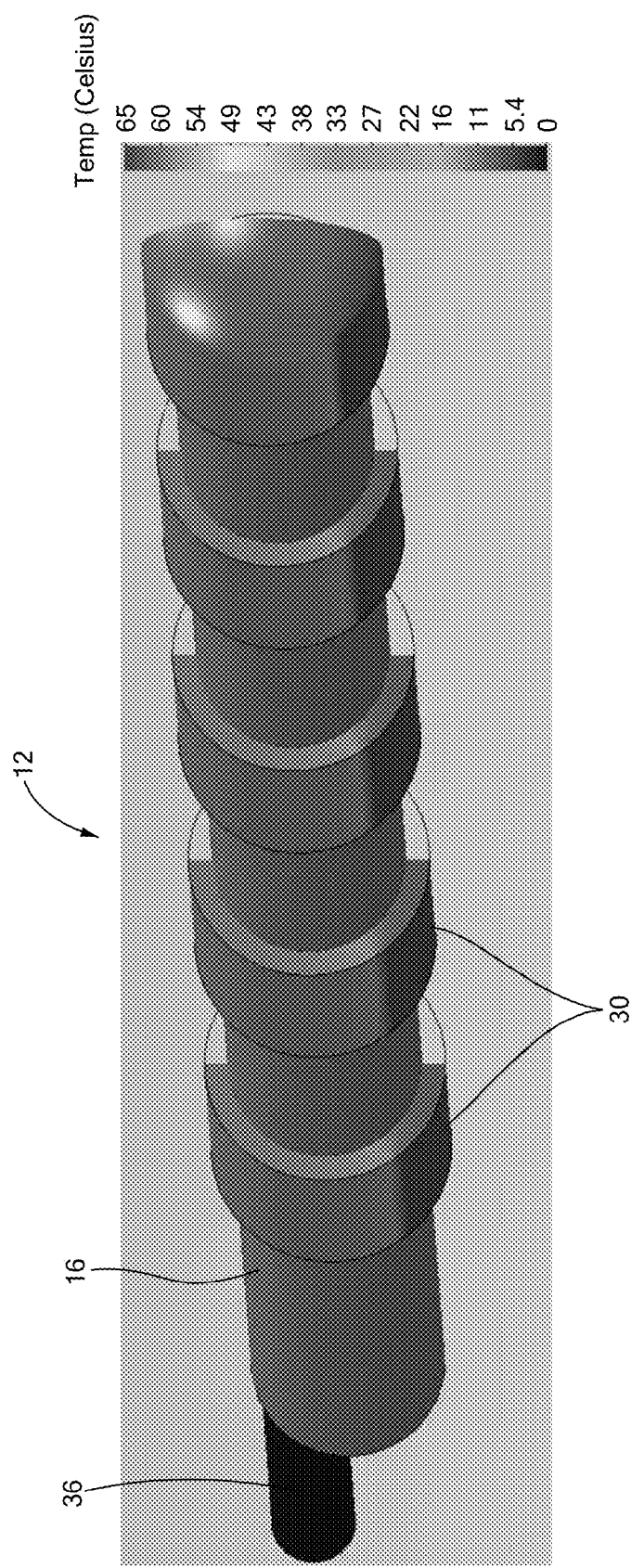
FIG. 4 is a graphical representation of temperature distribution in a medical device of the system of FIG. 1.
Figure 5:
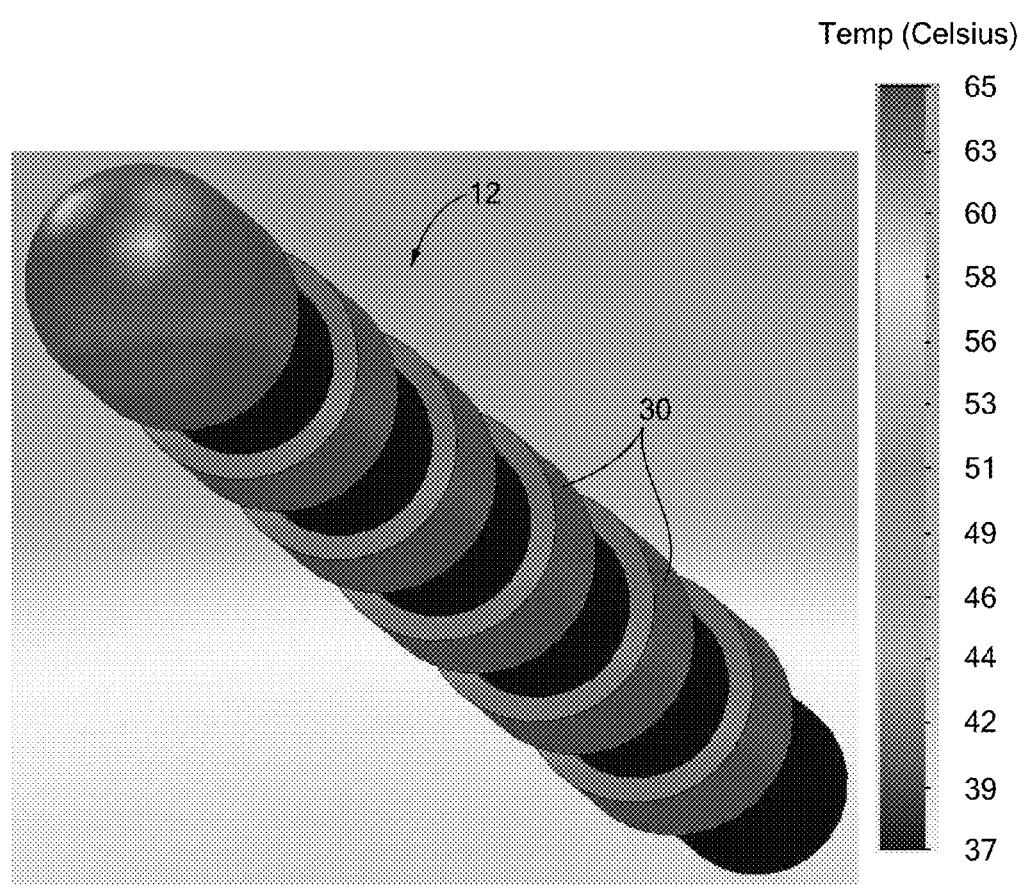
FIG. 5 is an additional graphical representation of temperature distribution in a medical device of the system of FIG. 1.

As shown in FIGS. 4-5, the heat transfer element 36 provides an effective avenue for heat transfer, allowing significant temperature reductions in portions of the electrodes 30 and medical device. Isolating the electrodes 30 and/or the temperature sensors 34 from the fluid flow and positioning the heat transfer element 36 away from the tissue-device interface allows the electrodes 30 to be cooled without compromising the accuracy of the temperature sensor 34 in measuring the actual electrode-tissue temperature where treatment is being delivered. This, in turn, prevents inaccurate or compromised temperature readings from being conveyed to the control unit 14, which may be programmed to adjust energy delivery in direct response to those measured temperatures.

It will be appreciated by persons skilled in the art that the present invention is not limited to what has been particularly shown and described herein above. In addition, unless mention was made above to the contrary, it should be noted that all of the accompanying drawings are not to scale. Of note, the device components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein. Moreover, while certain embodiments or figures described herein may illustrate features not expressly indicated on other figures or embodiments, it is understood that the features and components of the system and devices disclosed herein are not necessarily exclusive of each other and may be included in a variety of different combinations or configurations without departing from the scope and spirit of the invention. Indeed, a variety of modifications and variations are possible in light of the above teachings without departing from the scope and spirit of the invention, which is limited only by the following claims.

What is claimed is:

1. A medical device, comprising:

A catheter defining a distal portion, a proximal portion, and a fluid flow path through at least a portion of the proximal portion, the distal portion and proximal portion being separated by a fluidically-sealing component disposed within the catheter;

at least one electrode disposed on the distal portion of the catheter;

a temperature sensor proximate the electrode; and a heat transfer element defining a first portion disposed within the distal portion of the catheter in thermal communication with the electrode and a second portion disposed within the proximal portion of the catheter in thermal communication with the fluid flow path, at least a portion of the heat transfer element passing through the fluidically-sealing element, at least one of the electrode and temperature sensor being isolated from the fluid flow path.

2. The medical device of claim 1, wherein the heat transfer element includes an elongated heat sink.

3. The medical device of claim 1, wherein the heat transfer element is asymmetrically positioned about a longitudinal axis of the catheter.

4. The medical device of claim 1, wherein the fluid flow path includes a fluid injection conduit and a fluid exhaust lumen.

5. The medical device of claim 1, further comprising a coolant source coupled to the fluid flow path.

6. The medical device of claim 5, wherein the coolant source contains a cryogenic fluid.

7. The medical device of claim 5, further comprising a vacuum source coupled to the fluid flow path.

8. The medical device of claim 1, further comprising an electrical power source coupled to the electrode.

9. The medical device of claim 8, wherein the electrical power source is a radiofrequency signal generator.

10. A medical system, comprising:

a catheter having a proximal portion, a distal portion, and a fluid flow path through at least a portion of the proximal portion, the distal portion and the proximal portion being fluidly isolated by a separation component disposed within the catheter;

a plurality of electrodes on the distal portion;

at least one temperature sensor coupled to the distal portion;

an elongate heat transfer element defining a first portion disposed within the distal portion of the catheter in thermal communication with each electrode and defining a second portion disposed within the proximal portion of the catheter in thermal communication with the fluid flow path, at least a portion of the heat transfer element passing through the separation component; and a radiofrequency signal generator in communication with the plurality of electrodes, the radiofrequency signal generator programmed to modulate radiofrequency energy delivery to the plurality of electrodes based at least in part on a signal from the at least one temperature sensor.

11. The system of claim 10, wherein the distal portion defines a circumference having a first portion thereof that is a tissue contact side, and a second portion thereof that is a non-contact side opposite the tissue contact side, and wherein the elongate heat transfer element is positioned within the distal portion adjacent the non-contact side.

12. The system of claim 10, wherein the heat transfer element is asymmetrically positioned about a longitudinal axis of the catheter.

13. The system of claim 10, wherein the fluid flow path includes:

a fluid injection tube disposed within the proximal portion of the catheter;

a fluid exhaust lumen disposed within the proximal portion of the catheter; and a fluid source in fluid communication with the fluid injection tube.

14. The system of claim 13, wherein the distal portion of the catheter is fluidly isolated from the fluid flow path.

15. The system of claim 13, wherein the plurality of electrodes are fluidly isolated from the fluid flow path.

16. The system of claim 13, wherein the at least one temperature sensor is fluidly isolated from the fluid flow path.

17. The system of claim 10, wherein at least a portion of the fluid flow path is wound about at least a portion of the second portion of the elongate heat transfer element within the proximal portion of the catheter.

18. A medical system, comprising:

a catheter having a distal portion, a proximal portion, a fluid flow path at least partially disposed within the proximal portion, and a longitudinal axis, the distal portion separated from the fluid flow path by a separation element disposed within the catheter;

a plurality of electrodes coupled to the distal portion;

at least one temperature sensor coupled to the distal portion;

a heat sink asymmetrically positioned within the catheter relative to the longitudinal axis and in thermal communication with each electrode and in thermal communication with the fluid flow path, at least a portion of the heat sink extending through the separation element from the proximal portion to the distal portion; and a radiofrequency signal generator in communication with the plurality of electrodes.

19. The system of claim 18, wherein the radiofrequency signal generator is programmed to adjust radiofrequency energy delivery to the plurality of electrodes based at least in part on feedback from the at least one temperature sensor.

20. The system of claim 18, further comprising a fluid source in fluid communication with the fluid flow path.

* * * * *